US010876157B2

(12) United States Patent
Drndic et al.

(10) Patent No.: US 10,876,157 B2
(45) Date of Patent: Dec. 29, 2020

(54) INSULATED NANOELECTRODE-NANOPORE DEVICES AND RELATED METHODS

(71) Applicant: The Trustees of The University of Pennsylvania, Philadelphia, PA (US)

(72) Inventors: Marija Drndic, Philadelphia, PA (US); Ken Healy, Auburn, AL (US); Vishva Ray, Ann Arbor, MI (US); Lauren J. Willis, Philadelphia, PA (US); Neil Peterman, Cambridge, MA (US); John Bartel, Palo Alto, CA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/429,655

(22) PCT Filed: Sep. 26, 2013

(86) PCT No.: PCT/US2013/061953
§ 371 (c)(1),
(2) Date: Mar. 19, 2015

(87) PCT Pub. No.: WO2014/052616
PCT Pub. Date: Apr. 3, 2014

(65) Prior Publication Data
US 2015/0232923 A1    Aug. 20, 2015

Related U.S. Application Data

(60) Provisional application No. 61/706,271, filed on Sep. 27, 2012.

(51) Int. Cl.
*G01N 27/40* (2006.01)
*C12Q 1/6869* (2018.01)
(Continued)

(52) U.S. Cl.
CPC ............ *C12Q 1/6869* (2013.01); *C23C 14/34* (2013.01); *C23C 16/45525* (2013.01); *G01N 27/40* (2013.01); *G01N 33/48721* (2013.01)

(58) Field of Classification Search
CPC ........ G01N 33/48721–48728; B03C 5/00–028
(Continued)

(56) References Cited

U.S. PATENT DOCUMENTS 7,811,479 B2    10/2010    Drndic et al.
7,813,160 B2    10/2010    Drndic
(Continued)

FOREIGN PATENT DOCUMENTS

WO    WO-2002-099878    12/2002
WO    WO-2006-076036    7/2006
(Continued)

OTHER PUBLICATIONS

Branton et al, "The Potential and Challenges of Nanopore Sequencing", Nature Biotechnology, Oct. 2008, 26, 1146-1153.
(Continued)

*Primary Examiner* — Bach T Dinh
(74) *Attorney, Agent, or Firm* — BakerHostetler (57) ABSTRACT

Disclosed are insulated nanoelectrode associated with nanopores, useful in macromolecular analysis devices. Also disclosed are related methods of fabrication and use.

17 Claims, 5 Drawing Sheets

(51) Int. Cl.
   *G01N 33/487* (2006.01)
   *C23C 14/34* (2006.01)
   *C23C 16/455* (2006.01)

(58) Field of Classification Search
   USPC .............. 204/450–470, 547–549, 600–621, 204/644–648
   See application file for complete search history.

(56) References Cited

U.S. PATENT DOCUMENTS

| | | | |
|---|---|---|---|
| 7,887,720 | B2 | 2/2011 | Drndic et al. |
| 8,173,335 | B2 | 5/2012 | Drndic |
| 2004/0099901 | A1* | 5/2004 | Ludwig ............ H01L 27/11521 257/315 |
| 2007/0172386 | A1* | 7/2007 | Li ..................... C01N 33/48721 422/68.1 |
| 2008/0171316 | A1* | 7/2008 | Golovchenko ...... C12Q 1/6869 435/6.11 |
| 2010/0009134 | A1 | 1/2010 | Drndic |
| 2012/0037919 | A1* | 2/2012 | Xu ........................ B82Y 15/00 257/76 |
| 2013/0092541 | A1 | 4/2013 | Drndic et al. |
| 2014/0174927 | A1* | 6/2014 | Bashir .................. C12Q 1/6827 204/452 |

FOREIGN PATENT DOCUMENTS

| | | |
|---|---|---|
| WO | WO-2006-102292 | 9/2006 |
| WO | WO-2008-092760 | 8/2008 |
| WO | WO-2009-035647 | 3/2009 |
| WO | WO-2009-045473 | 4/2009 |
| WO | WO2011047582 * | 4/2011 |
| WO | WO-2011-103424 | 8/2011 |
| WO | WO2011103424 * | 8/2011 |

OTHER PUBLICATIONS

Chang et al, "Electronic Signatures of all Four DNA Nucleosides in a Tunneling Gap", Nano. Letters, Feb. 8, 2010, 10(3), 1070-1075.
Chang et al, "Tunnel Conductance of Watson-Crick Nucleoside-Base Pairs from Telegraph Noise", Nanotechnology May 6, 2009, 20, 185102.
Chang et al, "Tunneling Readout of Hydrogen-Bonding Based Recognition", National Nanotechnology, May 2009, 4(5), 297-301.
Chen et al, "Atomic Layer Deposition to Fine-Tune the Surface Properties and Diameters of Fabricated Nanopores", Nano Letters, Jun. 25, 2004, 4(7), 1333-1337.
Chen et al,, "First-Principles Study of High Conductance DNA Sequencing With Carbon Nanotube Electrodes", Phys. Rev. B., Mar. 2012, 85, 115436.
Cherf et al, "Automated Forward and Reverse Ratcheting of DNA in a Nanopore at Five Angstrom Precision", Nat. Biotechnol. Feb. 2012, 30, 344-348.
Danelon et al, "Fabrication and Functionalization of Nanochannels by Electron-Beam-Induced Silicon Oxide Deposition", Sep. 2006, 22, 10711-10715.
Deamer, D. W.and , Akeson, M., "Nanopores and Nucleic Acids: Prospects for Ultrarapid Sequencing", Trends Biotechnology, Apr. 2000, 18, 147-151.
Dekker, C., "Solid-State Nanopores", Nature. Nanotechnology, Apr. 2007, 2, 209-215.
Fischbein, M. D., Drndi' M., "Sub-10 nm Device Fabrication in a Transmission Electron", Microscope, Nano Letters, Apr. 2007, 7(5), 1329-1337.
Grant et al, "Transmission Electron Microscopy'windows' for Nanofabricated Structures", Nanotechnology, Jul. 16, 2004, 15(9), 1175-1181.
Harrer et al, "Electrochemical Protection of Thin Film Electrodes in Solid State Nanopores", Nanotechnology, Jul. 8, 2011, 22(27), 275304.

He et al, "Identification of DNA Basepairing via Tunnel-Current Decay", Nano Letters, Nov. 28, 2007, 7(12), 3854-3858.
He et al, "Transverse Tunneling Through DNA Hydrogen Bonded to an Electrode", Nano Lett. Aug. 2008, 8(8), 2530-2534.
Healy et al, "Solid-State Nanopore Technologies for Nanopore-Based DNA Analysis", Nanomedicine, Dec. 2007, 2(6), 875-897.
Healy, "Fabrication and Characterization of Nanopores With Insulated Transverse Nanoelectrodes for DNA Sensing in Salt Solution", Electrophoresis, Dec. 2012, 33(23), 3488-3496.
Healy, K., "Nanopore-Based Single-Molecule DNA Analysis", Nanomedicine, Aug. 2007, 2(4), 459-481.
Huang et al, , "Identifying Single Bases in a DNA Oligomer With Electron Tunnelling", Nature Nanotechnology, Dec. 2010, 5(12), 868-873.
Huang et al, "Recognition Tunneling Measurement of the Conductance of DNA Bases Embedded in Self-Assembled Monolayers", Journal of Physical Chemistry C Nanomater Interfaces, Dec. 9, 2010, 114(48), 20443-20448.
International Application No. PCT/US2013/061953: International Search Report and Written Opinion dated Jan. 10, 2014, 8 pages.
Ivanov et al, "DNA Tunneling Detector Embedded in a Nanopore", Nano Letters, Jan. 12, 2011, 11(1), 279-285.
Jiang et al, "Fabrication of nanopores with embedded annular electrodes and transverse carbon nanotube electrodes", Journal of Physics: Condensed Matter, Oct. 29, 2010, 22, 454114.
Krapf et al. "Fabrication and Characterization of Nanopore-Based Electrodes With Radii Down to 2 nm", Nano letters, Dec. 8, 2005, 6(1), 105-109.
Krems et al, "Effect of Noise on DNA Sequencing via Transverse Electronic Transport", Biophysical Journal, Oct. 7, 2009, 97(7), 1990-1996.
Lagerqvist et al, "Fast DNA Sequencing via Transverse Electronic Transport", Nano Letters, Apr. 2006, 6(4), 779-782.
Liang, X and Chou, S.Y., "Nanogap Detector Inside Nanofluidic Channel for Fast Real-Time Label-Free DNA Analysis", Nano Letters, May 2008, 8(5), 1472-1476.
Manrao et al, "Reading DNA At Single-Nucleotide Resolution With a Mutant MspA nanopore and phi29 DNA Polymerase", Nature Biotechnology, Mar. 2012, 30(4), 349-353.
Merchant et al, "DNA Translocation Through Graphene Nanopores", Nano letters., Jul. 23, 2010, 10(8), 3163-3167.
Meunier, V., Krsti 'P. S., "Enhancement of the Transverse Conductance in DNA Nucleotides", The Journal of Chemical Physics, Jan. 2008, 128, 041103.
Nelson et al, "Detection of Nucleic Acids with Graphene Nanopores: Ab Initio Characterization of a Novel Sequencing Device", Nano Letters, Sep. 8, 2010, 10(9), 3237-3242.
Polonsky et al, "Nanopore in metal-dielectric sandwich for DNA position control", Applied Physics Letters, Oct. 2007, 91(15), 153103.
Postma, H. W. Ch., "Rapid Sequencing of Individual DNA Molecules in Graphene Nanogaps", Nano Letters, Jan. 4, 2010, 10(2), 420-425.
Saha et al, "DNA Base-Specific Modulation of Microampere Transverse Edge Currents Through a Metallic Graphene Nanoribbon With a Nanopore", Nano Letters, Jan. 11, 2012, 12(1), 50-55.
Smeets et al, "Nanobubbles in Solid-State Nanopores", Physical Review Letters, Aug. 24, 2006, 97(8), 088101.
Smeets, "Salt Dependence of Ion Transport and DNA Translocation Through Solid-State Nanopores", Nano letters. Dec. 13, 2005, 6(1); 89-95.
Storm et al,, "Fabrication of Solid-State Nanopores With Single-Nanometre Precision", Nature Materials, Aug. 2003, 2, 537-540.
Tabard-Cossa et al, "Noise Analysis and Reduction in Solid-State Nanopores", Nanotechnology, Jun. 29, 2007, 18(30), 305505.
Tanaka, H., and Kawai, T., "Partial Sequencing of a Single DNA Molecule With a Scanning Tunnelling Microscope", Nature Nanotechnology, Jul. 5, 2009, 4, 518-522.
Tsutsui et al, "Electrical Detection of Single Methylcytosines in a DNA Oligomer", Journal of the American Chemical Society, Jun. 15, 2011, 133(23), 9124-9128.
Tsutsui et al, "Identifying Single Nucleotides by Tunnelling Current", Nanotechnology, Apr. 2010, 5, 286-290.

(56) References Cited

OTHER PUBLICATIONS

Tsutsui et al, "Single-Molecule Sensing Electrode Embedded In-Plane Nanopore", Scientific. Reports, Jul. 28, 2011, 1, 46.
Tuchband et al, "Insulated gold scanning tunneling microscopy probes for recognition tunneling in an aqueous environment", Review of Scientific Instruments, Jan. 2012, 83(1), 015102-1-015102-4.
Venkatesan, B. M., and Bashir, R., "Nanopore Sensors for Nucleic Acid Analysis", Nature Nanotechnology, Oct. 2011, 6, 615-624.
Wanunu, M., and Meller, A., "Chemically Modified Solid-State Nanopores", Nano Letters, Jun. 2007, 7(6), 1580-1585.
Wanunu, M., "Nanopores: A Journey Towards DNA Sequencing", Physics of Life Reviews, Jun. 2012, 9(2), 125-158.
Xie et al, "Local Electrical Potential Detection of DNA by Nanowire-Nanopore Sensors", Nature Nanotechnology, Feb. 2012, 7, 119-125.
Zwolak, M. and Di Ventra, M., "Electronic Signature of DNA Nucleotides via Transverse Transport", Nano Letters,. Mar. 2005, 5(3), 421-424.

\* cited by examiner

INSULATED NANOELECTRODE-NANOPORE DEVICES AND RELATED METHODS

CROSS-REFERENCE TO RELATED APPLICATIONS

This application is the National Stage Entry of International Application No. PCT/US2013/061953, filed Sep. 26, 2013, which claims the benefit of and priority to U.S. Patent Application No. 61/706,271, filed Sep. 27, 2012. The entire disclosures of all foregoing applications are incorporated herein by reference in their entireties for any and all purposes.

GOVERNMENT RIGHTS

This invention was made with government support under Grant No. R21HG004767 awarded by the National Institutes of Health and the American Recovery and Reinvestment Act Supplement to that Grant. The government has certain rights in the invention.

TECHNICAL FIELD

The present disclosure relates to the field of nanofabricated solid-state devices and to the field of DNA sequencing analysis.

BACKGROUND

Nanometer-sized pores in thin membranes are one candidate for DNA sequencing analysis. The basic concept involves placing a chamber of electrolyte solution on either side of the nanopore and applying a voltage between the chambers. This drives a flux of ions through the pore, which can be measured as a current flowing in the circuit. DNA molecules placed in the cathodic chamber are driven through the pore by their charge, blocking the ionic current as they pass through. With an appropriately sized pore, the DNA molecule is forced to move through in single-file, and thus the current blockage corresponds to the local structure of the DNA molecule along its length, and ultimately its sequence.

However, DNA molecules move through the nanopore so quickly that any differences in current due the DNA sequence is swamped by noise from the amplifier electronics and the thermal motion of ions, which presents a challenge to existing pore-based technologies. Accordingly, there is a need in the art for improved devices for macromolecular analysis.

SUMMARY

The present disclosure provides, inter alia, nanopores in formed in membranes (e.g., silicon nitride membranes) having aligned nanoelectrodes for transverse sensing across the pore aperture. This includes fabricating these devices, imaging them by transmission electron microscopy, and testing their electrical characteristics in solution (e.g., salt solutions). Also disclosed is insulating the nanoelectrodes, while optionally keeping the electrodes' tips exposed, as well as processes for accomplishing this. Further disclosed is the effect of nanoelectrodes and insulation on nanopore stability or DNA translocation, as observed in the ionic current signal measured using macroscopic electrodes.

In one embodiment, the present disclosure provides macromolecule analysis components, comprising: a substrate having an upper surface surmounted by a layer of a first material; a layer of a second material surmounting the layer of the first material; two electrodes surmounting the layer of second material, the two electrodes having ends separated at least in part by an aperture extending through the layer of second material, and at least one of the electrodes being at least partially surrounded by an insulating material.

Also provided are methods, comprising: translocating a macromolecule through the aperture of a macromolecule analysis component according to the present disclosure and collecting a signal related to the translocation.

Further provided are methods of fabricating a macromolecule analysis component, comprising: forming a membrane atop a support that is disposed atop a substrate; forming electrodes separated by the aperture of the membrane; disposing an insulating material atop the electrodes; forming an aperture in the membrane; and forming an aperture in the substrate, the aperture being in fluid communication with the aperture of the membrane.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 1. (A) Transverse sensing concept. DNA molecules are driven through the nanopore by an electric field applied via macroscopic electrodes, and the DNA bases modulate the transverse signal between the nanoelectrodes as they pass between them. (B) Diagram showing a cross-section of a silicon nitride membrane chip with a nanopore, nanoelectrodes, and insulation. The inset shows a magnified view of the nanopore area. (C) Photograph of an actual chip, where the contact pads used to interface with the nanoelectrodes can be seen. The titanium dioxide insulation layer is also faintly visible as a tinge over the connecting traces. It has been removed over the contact pads.

FIG. 2. (A-C) Finite element simulations of the current density for a potential difference of 1 V between the nanoelectrodes, without (A, dashed line in C) and with (B, solid line in C) insulation. The nanopore is ca. 5 nm in diameter, the electrodes are 2-nm high, 5-nm wide, and have flat faces terminating at the pore edge. Each nanoelectrode is 2 micrometers long. The insulation (if present) is 3-nm thick and covers all but the end face of the nanoelectrodes. The solution conductivity is 1 S/m. Note that the vertical axis is the same for (A-C). (D) Diagram showing how plots (A-C) are oriented. (A, B) are plots on the dark plane intersecting the membrane. The lighter rectangle on this plane is a projection of the electrode cross-section. The fraction of the total current flowing through this rectangle is quoted in the text. The curves in (C) are plots on the dashed line running along the nanopore axis. (E) TEM image of nanoelectrodes with titanium dioxide insulation. The contrast of this image is amplified to highlight the titanium dioxide layer. (F) Leakage current for uninsulated (squares) and insulated (circles) electrodes, with the low leakage in the latter case highlighted in the left inset. The right inset shows the measurement configuration. This measurement was carried out in 1 M KCl, 10 mM Tris, 1 mM EDTA, pH 8.5.

FIG. 3. (A-F) TEM images of a range of nanoporenanoelectrode devices. The distance between the nanoelectrodes in these devices ranges from 2.5 to 30 nm. Dark areas are gold (on a nickel, titanium, or nichrome adhesion layer), lighter gray is the silicon nitride membrane, and the light circles between the gold nanoelectrodes are nanopores through the silicon nitride membrane. All scale bars are 10 nm. (G) Optical microscope image showing a silicon nitride membrane with 12 pairs of nanoelectrodes and associated connecting traces.

FIG. 4. The presence of nanoelectrodes and insulation do not affect the ionic current through the nanopore (A), or the characteristics of DNA translocation (B-D). (B) Nanopore in a bare silicon nitride membrane without nanoelectrodes, (C) nanopore with uninsulated nanoelectrodes, (D) nanopore- with insulated nanoelectrodes. (E) Noise power spectral density plots of the ionic current measured without DNA, for the same nanopore devices as in (A-D). The left-hand regions of the plots that decrease with frequency are 1/f noise, commonly associated with fluctuations in wetting of the nanopore surface. The right-hand regions that increase with frequency are due to the voltage noise of the amplifier scaled by the membrane capacitance. The spikes in these plots are all due to external interference, mainly from switching power supplies in computer equipment. Each spike is confined to a very narrow frequency band, so the spikes do not contribute significantly to the total noise. All measurements were carried out with 120 mV bias voltage, using 1 M KCl, 10 mM Tris, 1 mM EDTA, at pH 8.5-9.0. For DNA translocation experiments, 15 kbp DNA was added to this solution.

FIG. 5. (A) Optical microscope image of a silicon nitride membrane that ruptured due to mechanical shock. This membrane is much larger than those used for nanopore experiments. It is shown here because its size illustrates the characteristics of rupture very clearly, but smaller membranes rupture in the same way. (B, C) TEM images of ruptures caused by electrostatic discharge between nanoelectrode tips. The difference between the smooth edge of the rupture characteristic of electrostatic discharge, compared to the jagged edge associated with mechanical shock. In the case of electrostatic discharge, the membrane may also have fractures in the radial direction, as in (C). (D) TEM image of a nanopore-nanoelectrode device after measurement in solution that did not rupture due to mechanical shock or electrostatic discharge, but where the nanoelectrode tips have disappeared. The dashed lines show the original footprints of the nanoelectrodes.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value.

Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range. Any and all documents cited in this application are incorporated herein by reference in their entireties.

In one embodiment, the present disclosure provides macromolecule analysis components. These components suitably include a substrate having an upper surface surmounted by a layer of a first material; a layer of a second material surmounting the layer of the first material; two electrodes surmounting the layer of second material, the two electrodes having ends separated at least in part by an aperture extending through the layer of second material, and the two electrodes being surmounted by an insulating material. It should be understood that the first material and second materials are not required, as devices may comprise a substrate surmounted by a first material and electrodes surmounting that first material. As described elsewhere herein, at least one electrode may be at least partially surmounted by an insulating material.

The electrodes may suitably be separated by less than about 1000 nm, by less than about 100 nm, by less than 10 nm or even less than 5 nm or less than 2.5 nm. The electrodes may be collinear with one another or may be offset; the electrodes may suitably face one another as shown in, e.g., FIG. 1 and FIG. 2. The electrodes may be linear or bar-like in shape, but may also be curved, tapered, or even be polygonal. The electrodes' tips may be rounded, squared, jagged, notched, or even pointed. It should be understood that the electrodes need not be of the same shape, composition, or thickness. An electrode may define a cross-sectional dimension (e.g., thickness, width) in the range of from about 1 nm to about 1000 nm, from about 10 nm to about 500 nm, from about 20 nm to about 100 nm, or even about 50 nm. Electrodes having a cross-sectional dimension in the range of from about 1 nm to about 10 nm are considered suitable.

Silicon in one or more forms (or in a mixture with one or more other elements) is considered a suitable substrate or even insulator for these components, although other materials may be used. The substrate is suitably from about 10 microns to about 10 millimeters in thickness, or from about 5 microns to about 500 microns, or even from about 10 microns to about 50 microns. Substrates having a thickness of greater than 100 microns (e.g., 1000 microns, 10,000 microns, 100,000 microns, or more) are also suitable. Comparatively thin substrates—such as those having a thickness of from about 5 nm to about 1000 nm are also suitable; substrates having a thickness in the range of 30 nm to about 70 nm are especially suitable.

The first material may be, e.g., silicon dioxide, as well as silicon-dioxide-based glasses such as borosilicate glass, fused silica, and quartz glass. Other insulators are suitable first materials, including materials that are capable of forming a freestanding membrane, including silicon nitride, aluminum oxide, hafnium oxide, and silicon dioxide. The first material may have a thickness in the range of from about 10 nm to about 1 mm.

The second material may be, e.g., silicon nitride, although other insulators are suitable, including: aluminum oxide, hafnium oxide, silicon dioxide, and other materials capable of forming a freestanding membrane. Thicknesses for the second material in the range of from 1 nm to 150 nm, 200 nm, or even 1000 nm are suitable.

The aperture may have a cross-sectional dimension in the range of from about 0.5 nm to about 100 nm. An aperature may be circular in cross-section, but may also be oblong, slit-shaped, polygonal, otherwise irregular in shape.

An insulator material may include a variety of materials known to those of ordinary skill in the art, e.g., silicon (in elemental form or in other form, including mixed with other elements), oxide (e.g., titanium dioxide, aluminum oxide, hafnium oxide), and combinations thereof. Insulating material may have a thickness in the range of from about 1 nm to about 50 nm, about 100 nm, or even about 500 nm. Insulating material may be present with a thickness of one or more atomic layers, particularly in embodiments where the insulating material is deposited via atomic layer deposition. The insulating material suitably surmounts at least some of the exposed material of an electrode; in some embodiments, the entirety of the exposed material of the electrode is surmounted by the insulating material. In other embodiments, only a portion (e.g., the tip) is exposed while the remainder of the material remains surmounted by the insulating material. The insulating material may surmount from 100% to about 0.001% of the exposed area of the electrode, or from 90% to about 0.1%, or from 75% to about 1%, or even from 50% to about 5% of the exposed area of the electrode. It should be understood that in a device that has multiple electrodes, different electrodes may be surmounted by insulating materials that differ in composition, dimension, or both.

The substrate may have a second surface, which surface may be surmounted by a second layer of the first material. The second layer of the first material may be surmounted by a second layer of the second material.

Components may further include an adhesion material disposed between at least one electrode and the second material. This adhesion material may be, e.g., titanium, nickel, or nichrome. The adhesion material may have a thickness in the range of from 1 nm to about 50 nm.

It should be understood that although the exemplary figures attached hereto depict a single aperture formed in a component, a component may feature two, three, or more apertures, which apertures may each be individually/separately addressed by electrodes. This enables parallel, multiplex analysis of a sample by using a single component.

The aperture formed in the layer of second material may, as shown in the attached figures, be in fluid communication with an aperture formed in the substrate.

The present disclosure also provides methods. These methods include translocating a macromolecule through the aperture of a macromolecule analysis component according the present disclosure, and collecting a signal related to the translocation. Such a signal may then be used to determine macromolecular structure, e.g., DNA sequence, polymer structure, and the like, by differentiating between the signals associated with passage of different bases or segments through aperture of the device.

Also provided are methods of fabricating a macromolecule analysis component. The methods may include forming a membrane atop a support that is disposed atop a substrate; forming an aperture in the membrane; forming an aperture in the substrate, the aperture being in fluid communication with the aperture of the membrane; forming electrodes separated by the aperture of the membrane; and disposing an insulating material atop the electrodes. Suitable materials for the foregoing and suitable dimensions for the foregoing are described elsewhere herein.

In one exemplary embodiment, one may fabricate electrodes and dispose insulation atop the electrodes and then form (e.g., by "drilling") an aperture hole through the insulation. The the foregoing steps need not be performed in any particular order. It is considered suitable, however, to first fabricate the electrodes, followed by disposing the insulation and then forming the aperture through the insulation. This in turn enables a user to expose the tips of the electrodes. Embodiments in which the electrode tips are exposed (while the remainders of the electrodes are surmounted by insulation) are considered particularly suitable.

Insulating material may be disposed, removed, or both, so as to leave exposed at least a portion of an electrode. As described elsewhere herein, electrodes may be separated by less than about 100 nm. Electrodes separated by about 10 nm, about 5 nm, or even about 2.5 nm are considered especially suitable.

An aperture may be formed by, e.g., ion beam, electron beam, transmission electron beam ablation lithography, or any combination thereof. Insulating material may be disposed by CVD, atomic layer deposition; one may also use thermal evaporation and/or sputtering for one or more of the foregoing steps. An electrode may be formed by methods known to those of ordinary skill in the art, e.g., electron beam lithography, thermal evaporation, or any combination thereof.

A user may further connect or more electrodes with a connecting trace, as described elsewhere herein. These traces may serve to prevent electrostatic discharge between the electrodes during device fabrication and storage. Connecting traces are suitably removed before the component is used in an analysis, as described in U.S. application Ser. No. 13/587,141, "High-Resolution Analysis Devices and Related Methods," filed Aug. 16, 2012, incorporated herein by reference in its entirety for any and all purposes.

A user may also apply a plasma (e.g., an oxygen plasma or other plasma), heating/annealing, ultraviolet light, ozone, or any combination thereof as part of the disclosed methods. Such application may assist in cleaning or otherwise conditioning the device before, during, or even after fabrication. Heating is suitably applied before nanoelectrode fabrication.

Various techniques useful for disposing materials and manipulating materials (e.g., by ablation, by ion beam, by electron beam, and the like) are known to those of skill in the art. Exemplary techniques are found in the following references, each of which is incorporated herein by reference in its entirety for any and all purposes: PCT/US2005/018342, "Nanostructure Assemblies, Methods, and Devices Thereof," filed May 25, 2005; PCT/US2006/010157, "Nanogaps: Methods and Devices Containing Same," filed Mar. 21, 2006; U.S. application Ser. No. 12/373,607, "Beam Ablation Lithography," filed Jan. 13, 2009; U.S. application Ser. No. 12/608,348, "Polymer-Nanocrystal Quantum Dot Composites and Optoelectronic Devices," filed Oct. 29, 2009; PCT/US2011/025434, "Devices and Related Methods of High-Resolution Analysis," filed Feb. 18, 2011; U.S. application Ser. No. 11/329,471, "Nanocrystal Quantum Dot Memory Devices," filed Jan. 11, 2006; U.S. application Ser. No. 11/348,039, "Polymer-Nanocrystal Quantum Dot Composites and Optoelectronic Devices," filed Feb. 6, 2006; and U.S. application Ser. No. 13/587,141, "High-Resolution Analysis Devices and Related Methods," filed Aug. 16, 2012.

Exemplary Non-Limiting Embodiments

The following are illustrative, non-limiting embodiments of the disclosed technology. None of the following embodiments should be understood as limiting the scope of the present disclosure.

Silicon Nitride Membrane Fabrication

Fabrication of silicon nitride membranes suspended on silicon support "chips" is known in the art. Here was used a modified version of this process to produce silicon nitride membranes (10-40 µm square) with a 5-µm silicon dioxide layer between the silicon nitride and silicon for reduced capacitance. The process involved growing 5 µm of silicon dioxide, by wet thermal oxidation, on each side of the (100) silicon wafer before low-stress (200-300 MPa) silicon nitride deposition, and additionally etching through these silicon dioxide layers with 6:1 buffered hydrofluoric acid (Transene, Danvers, Mass., USA). Appropriate safety precautions should be taken and extreme care used when working with hydrofluoric acid. A few drops of Triton X-100 surfactant (Sigma Aldrich, St. Louis, Mo., USA) per liter of buffered hydrofluoric acid were added to reduce the surface tension and avoid trapped air bubbles. One may optionally vapor prime the wafer with hexamethyldisilazane before spincoating photoresist, for both buffered hydrofluoric acid etch steps, to prevent the photoresist from peeling during the etch. In some embodiments that include a thick silicon dioxide layer, the layer may be flat but may also be bowed slightly upwards or even be curved downwards. The deformation may occur at the center and may be, e.g., approximately 1% of the membrane width. Silicon dioxide growth and silicon nitride deposition were provided as a service by the Cornell Nanoscale Science and Technology Facility, Ithaca, N.Y., USA. Subsequent fabrication was carried out at the University of Pennsylvania.

Nanoelectrode Fabrication

A two-stage process was used to fabricate nanoelectrodes, and contacts to connect to them with. The first step was to deposit the nanoelectrodes and fine connecting traces going to the edge of the silicon nitride membrane. This was achieved by a standard lift-off process. Briefly, the pattern to be deposited was defined in C2 950 PMMA resist (Microchem, Newton, Mass., USA) by electron beam lithography (ELS-7500EX, Elionix, Tokyo, Japan), an adhesion layer of nickel, titanium, or nichrome (5 nm) followed by a layer of gold (15 nm) was deposited on top by thermal evaporation (custom-built system, although any standard commercial evaporator will suffice), and then the resist was "lifted off" using acetone, leaving metal only in the pattern defined by the photoresist. Next, contact pads and coarse connecting traces to connect to the nanoelectrodes, were deposited using a similar lift-off process, using optical lithography (MA4 mask aligner, Suss Microtec, Sunnyvale, Calif., USA), instead of electron beam lithography. The photoresist used was NR7 (Futurrex, Franklin, N.J., USA).

Nanoelectrode Insulation

The nanoelectrodes were insulated by atomic layer deposition. A Savannah 200 system (Cambridge Nanotech, Cambridge, Mass., USA) was used to deposit 10 nm of titanium dioxide over the entire silicon nitride membrane chip. Subsequently, the titanium dioxide covering the contact pads was plasma etched away (Planar Etch II or PE II-A, Technics West, San Jose, Calif., USA, $SF_6+O_2$ mixture, approximately 600 mTorr pressure, 150 W, 1-3 min) so that electrical connections could be made. A second silicon nitride membrane chip was placed on top of the first chip to mask the areas not to be etched.

Nanopore Drilling and Nanoelectrode Shaping

The silicon nitride membrane chip with electrodes and insulation was then inserted into a JEOL 2010F field-emission TEM (JEOL USA, Peabody, Mass., USA). The nanoelectrode tips were fine-tuned, when desired, by nanosculpting them using a transmission electron beam ablation lithography technique. Then, a nanopore was drilled between the electrodes by the usual electron beam drilling approach. If a nanopore is drilled to intersect the electrode tips, insulation is removed there, allowing electrochemical conduction. For both transmission electron beam ablation lithography and nanopore drilling, the microscope was operated at 200 kV in standard TEM mode, with a 150-µm condenser aperture and maximum beam convergence angle (al mode).

At the start of each TEM session, the electron beam was aligned using the manufacturer-specified high-resolution alignment procedure while imaging a holey carbon sample. After loading each silicon nitride membrane chip, the alignment was checked. To ablate material, the target region was centered on the viewing screen at 500,000-1,000,000 times magnification, and the beam condensed to the tightest spot possible. Ablation occurs on the order of seconds for most metals, and minutes for silicon nitride, but depends on the microscope conditions and the particular material and its thickness. Ablation progress can be observed both as an increase in the beam current transmitted through the sample, and visually on the microscope's phosphor imaging screen; although the beam is maximally condensed, the intense central spot is surrounded by a weak halo, sufficient to view the ablation progress.

When the desired result was achieved, ablation was stopped by decondensing the beam. To ablate more than a single spot, the beam was manually shifted to ablate the desired pattern. Beam shift was also used to compensate for mechanical drift of the sample stage. In contrast to lighter metals such as silver, nickel, chrome, and aluminum, gold was not substantially ablated by the 200 kV electron beam due to its high atomic weight. Instead, beam exposure prompts the gold to crystallize. One may exploit this behavior to nanosculpt gold by directing the beam at an area adjacent to where material is to be removed. Without being bound to any theory, the resulting crystallization "pulls in" the gold, away from the target area. Note that a standard JEOL 2010F sample holder can only accommodate approximately 3×3 mm samples. This holder was modified by milling a larger recess to accommodate 5×5 mm silicon nitride membrane chips. The chips are placed membrane-side down into this holder so that the membrane is closest to the center of the microscope's focal range.

Ionic Current Measurements, DNA Translocation Experiments, and Nanoelectrode Measurements The nanopore chips were treated by UV/ozone (PSDP-UVT, Novascan, Ames, Iowa, USA, 80° C., 15 min each side) to facilitate wetting, and then mounted in a custom-made poly(dimethyl siloxane) measurement cell. Oxygen plasma treatment (Technics PE II-A, Technics West, San Jose, Calif., USA, 50 W, approximately 400 mT, 5 min, with the chip elevated to expose both sides) gave similar results. The cell had sub-millimeter width fluidic channels to limit the area of solution in contact with the chip surface, and thus the capacitance. The laminar solution flow imposed by these channels, together with the hydrophilic nature of poly(dimethyl siloxane), make the occurrence of trapped air bubbles rare. Cell channels were filled with a solution of 1 M KCl, 10 mM Tris, 1 mM EDTA at pH 8.5-9.0 (all chemicals from Sigma Aldrich). For DNA translocationmeasurements, 15 kbp Fermentas NoLimits ds-DNA fragments (Fermentas, Glen Burnie, Md., USA) were also added to the solution on the cathodic side. Ag/AgCl pellet electrodes (A-M Systems, Sequim, Wash., USA) made electrochemical connection to the solution, and an HEKA EPC10 triple channel patch clamp amplifier (HEKA Instruments, Bellmore, N.Y., USA) was used to apply voltage and measure and digitize current. Data were filtered using a 10 kHz 5-pole Bessel filter built into the EPC10 and digitized at 50 kHz. Custom software to record and analyze the data was written in LabVIEW (National Instruments, Austin, Tex., USA). For nanoelectrode measurements, the contact pads on the silicon nitride membrane chip were bonded to a custom designed 0.35-mm thickness printed circuit board (OurPCB, Shijiazhuang, China) using conductive silver paste. This enabled simultaneous fluidic and electrical connection to the chip. The circuit board plugs into a flat flexible cable connector on another circuit board, which is connected to the second channel of the EPC10 amplifier.

Exemplary Results

Figure 1A:
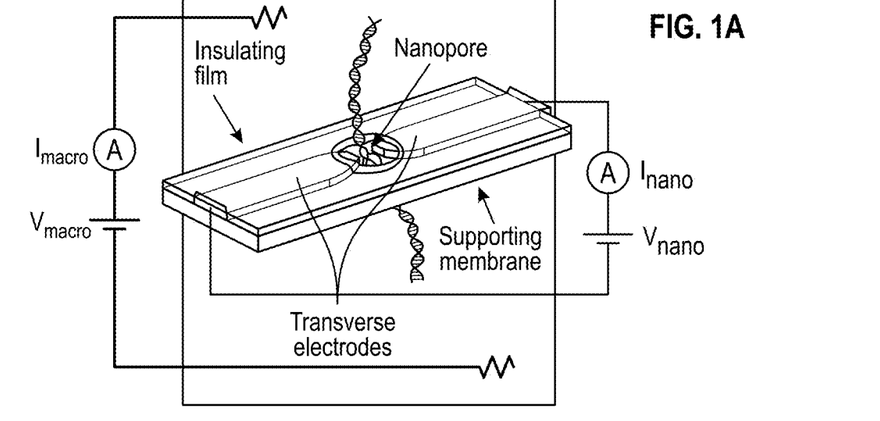
Figure 1B:
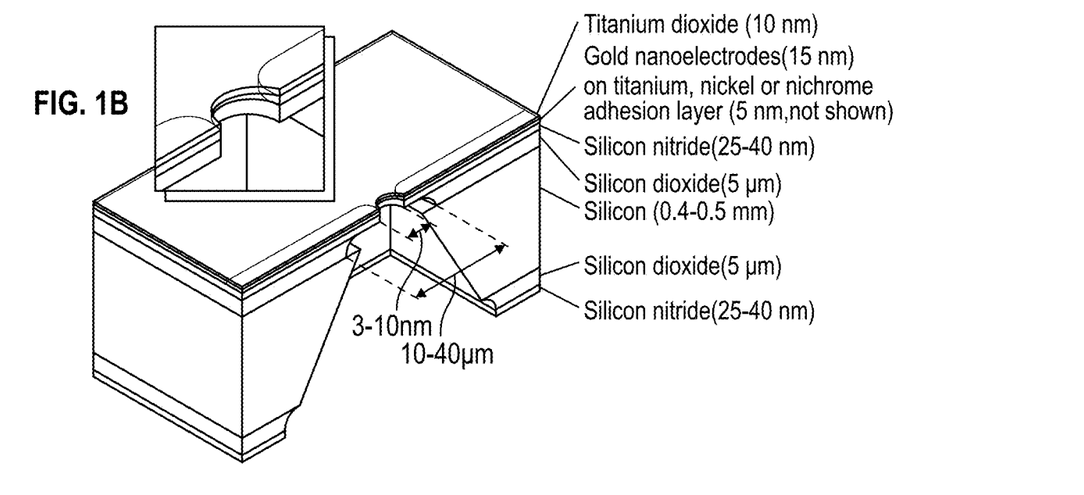
Figure 1C:
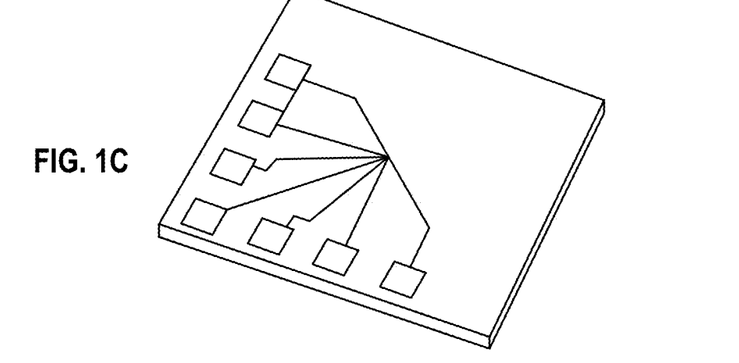

FIG. 1B shows a schematic of a silicon nitride membrane chip with a nanopore and insulated nanoelectrodes. FIG. 1C is a photograph of an actual 5×5 mm² chip where the contact pads and traces that connect to the nanoelectrodes can be seen. The titanium dioxide insulation layer is also faintly visible as a pinkish tinge over the connecting traces; the insulation has been removed over the contact pads.

Figure 2A:
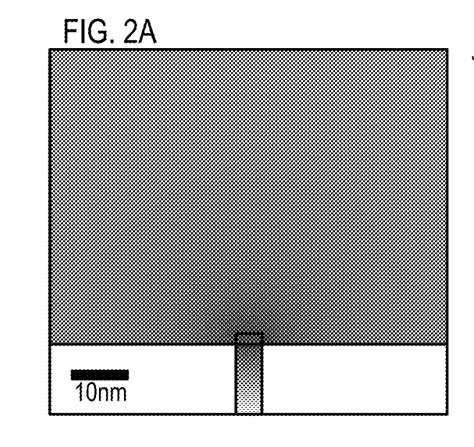
Figure 2B:
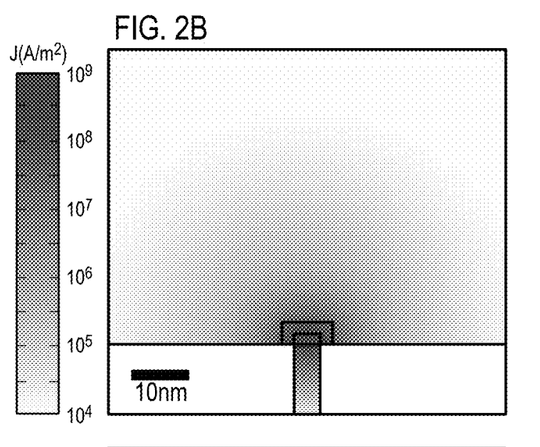
Figure 2C:
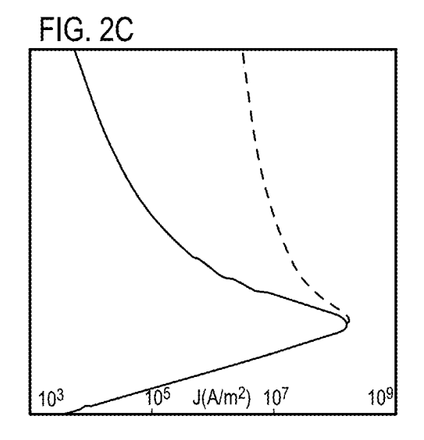
Figure 2D:
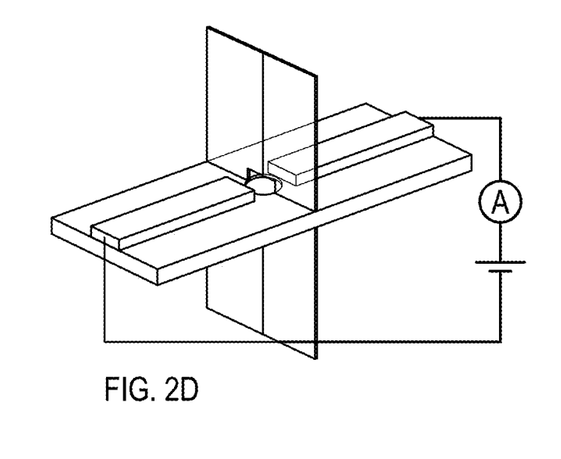

Insulating the nanoelectrodes is helpful to localize sensing to the nanoelectrode gap when measuring in electrolyte solution. Without being bound to a particular theory, with perfectly pure solutions, and pure gold electrodes, no electrochemical reactions take place at the voltages used (±100 mV). A leakage current flows (tens of nA at 25 mV), relative to that expected to flow just between the electrode tips. Thus, the current flowing between areas of the electrodes away from the tips swamps the signal of interest. FIG. 2A-C shows finite element simulations of current density, for a potential difference of 1 V applied between the electrodes, in a solution of conductivity 1 S/m. The nanopore was 5 nm in diameter, and electrodes are 2-nm high, 5-nm wide, and 2-μm long, with flat faces terminating at the pore edge. Where present, the insulation is 3-nm thick. Simulations were carried out using COMSOL Multiphysics (COMSOL, Burlington, Mass., USA). Without insulation (FIG. 2A, and dashed curve in FIG. 2C), the current density decays comparatively very slowly with distance from the nanoelectrodes. In fact, the fraction of the total current that flows through a rectangle the size of the electrode crosssection (see FIG. 2D) was negligible (<0.3%).

With insulation (FIG. 2B and solid curve in FIG. 2C), =current density decays more rapidly, and 25% of the total current flows through the same rectangle. The insulation may, in some embodiments, be thick enough to ensure uniform and complete coverage and sufficiently high resistance, but thin enough not to interfere with nanopore drilling. Ten nanometer thickness is suitable, although other thicknesses will also suffice.

Figure 2E:
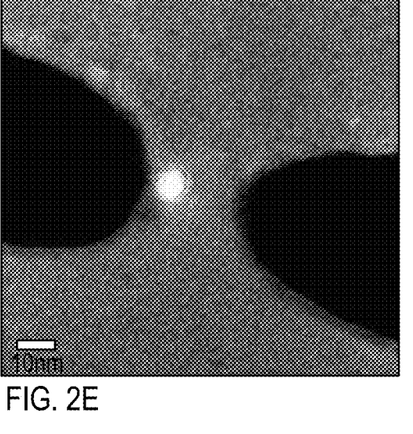
Figure 2F:
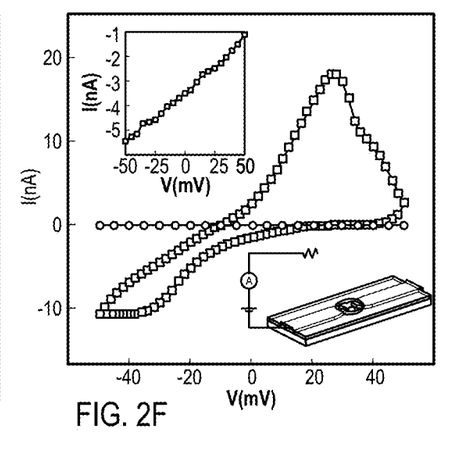

FIG. 2E shows a contrast-enhanced TEM image of insulated electrodes, where the titanium dioxide can be distinguished as a halo around the electrodes. This halo is not present without insulation. Without being bound to any particular theory, one may test the impact of the insulation by measuring the leakage current that flows from one of the nanoelectrodes to a macroscopic electrode inserted in the solution (see the inset in FIG. 2F). FIG. 2F highlights that the leakage current drops by several orders of magnitude to a few pA for insulated electrodes, over the voltage range tested.

Figure 3:
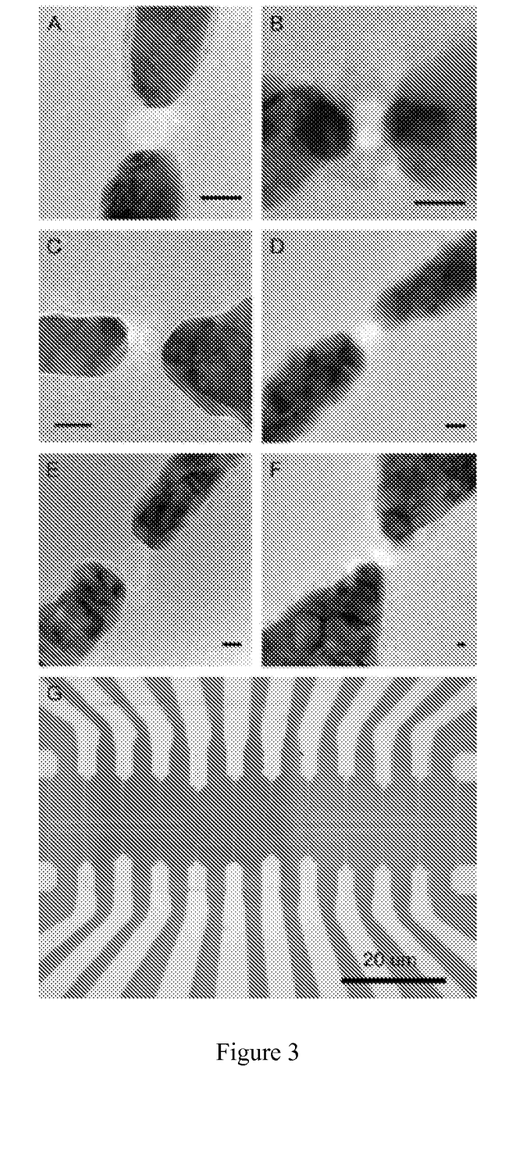

These nanopore devices with insulated nanoelectrodes can be produced reliably. FIG. 3A-F is TEM images of a range of devices with nanoelectrodes spaced from 2.5 to 30 nm. The distance between the nanoelectrodes in most of these devices is larger than that necessary to give a detectable tunneling current signal. Fabrication of small gaps to 1.5 nm and smaller may also be accomplished. One may fabricate multiple nanopores and nanoelectrodes on one silicon nitride membrane, for example, for sensing the same DNA sample in parallel. FIG. 3G shows a device with 12 pairs of nanoelectrodes.

Figure 4A:
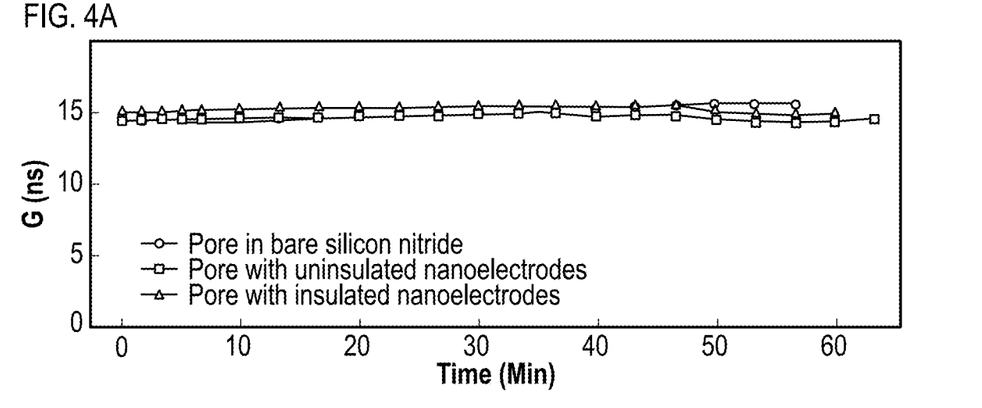
Figure 4B:
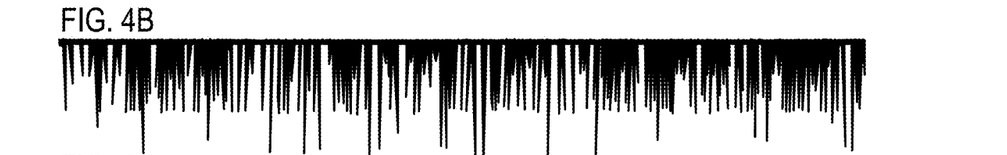
Figure 4C:
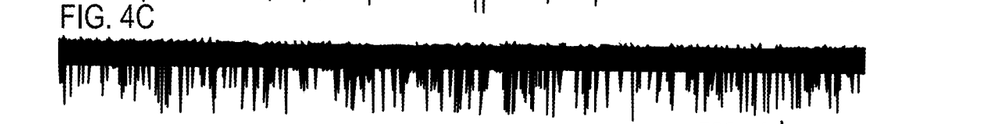
Figure 4D:
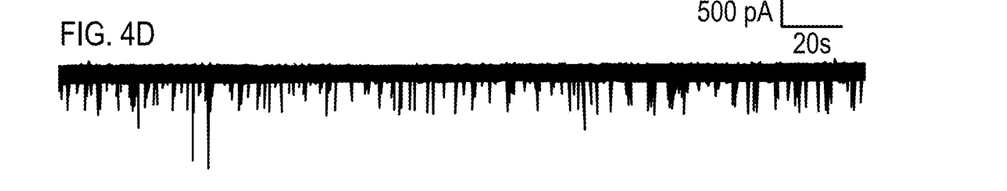

One may test to see if the presence of nanoelectrodes and insulation affect pore stability, as observed by measuring the ionic current between macroscopic electrodes. FIG. 4A shows the conductance of three different nanopores over a period of 60 min, one with insulated nanoelectrodes, one with bare nanoelectrodes, and the other in a bare silicon nitride membrane. All nanopores were approximately 6 nm in diameter. For all cases, the open-pore conductance remains constant around 15 nS, and there are no appreciable changes in stability over this period, which is much longer than the duration of typical nanopore sensing experiments (1-20 min) Similarly, DNA translocations are not affected. FIGS. 4B and D presents ionic current recordings taken using macroscopic electrodes. These show DNA translocations through each pore, again showing that there are no significant changes with electrodes or insulation, apart from the differences that are evident in this baseline noise level. One may observe that nanopores with insulated nanoelectrodes exhibit higher noise in the ionic current signal measured with macroscopic electrodes, compared to nanopores without nanoelectrodes. With bare nanoelectrodes, the noise is higher still. Without being bound to any theory, this is expected because the presence of nanoelectrodes increases the capacitance from one side of the membrane to the other. This capacitance scales the voltage noise of the amplifier electronics, which then contributes to the noise in the measured current. Therefore, higher capacitance means higher noise. Again without being bound to any particular theory, nanopore membranes can be reasonably approximated as parallel plate capacitors, whose capacitance is proportional to the plate area, and inversely proportional to the thickness of dielectric between the plates. The silicon support corresponds to one of the parallel plates, the silicon dioxide and silicon nitride layers are the dielectric, and the solution forms the other plate. (The silicon nitride membrane with no underlying silicon dioxide in the center of the chip can be ignored in this approximation, because its area is small compared to the total area).

Without nanoelectrodes, the capacitor plate area corresponds to the area of solution in contact with the SiN surface, in an exemplary case approximately 0.7 mm² However, with uninsulated nanoelectrodes, the solution is now electrically connected to the electrodes and their associated connecting traces and contact pads, which have a significantly larger area than that wetted by solution. Therefore, the capacitor plate area has expanded and the capacitance, and thus noise, goes up. With insulated electrodes, the additional capacitance due to the traces and contact pads outside the wetted area is in series with the capacitance from the solution through the insulation into the electrodes.

As series capacitances add reciprocally, this may result in a smaller increase in capacitance and noise compared to the case of bare electrodes. The impact of this capacitance can be seen more clearly in power spectral density plots.

Figure 4E:
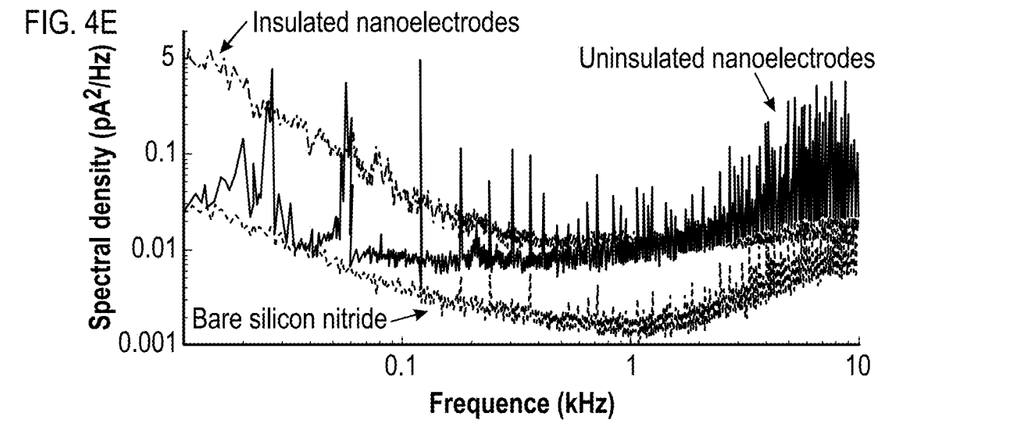
Figure 5:
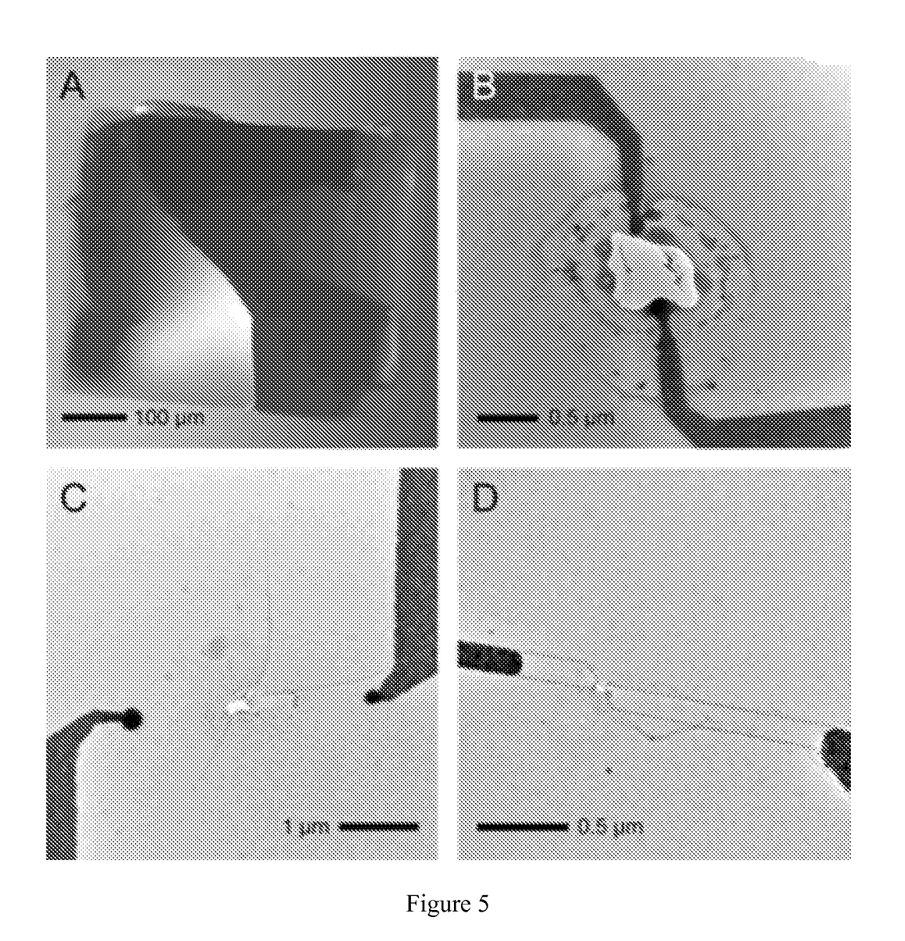

FIG. 4E shows power spectra of the ionic current signal measured with macroscopic electrodes for the same three nanopore devices in FIG. 4A-D. These were control measurements without any DNA, so the ionic current was steady, without any translocation events. The capacitance-scaled amplifier voltage noise is responsible for the rise in noise power with increasing frequency on the right-hand side of these plots. Higher noise in this region corresponds to higher capacitance; as as expected, the noise is highest with uninsulated nanoelectrodes and lowest for the nanopore in a bare silicon nitride membrane. The "1/f" sloped sections on the left-hand side of these plots are not related to the capacitance. High 1/f noise is commonly associated with poor wetting of the nanopore surface. Given the logarithmic nature of the plot, this 1/f component does not significantly influence the total noise, which was confirmed by computing the total rms noise as the integral of the spectral density with respect to frequency (not shown).

In some embodiments, one may connect nanoelectrode contact pads to each other with a narrow trace at the lithography stage. This ensures the electrodes are at the same potential, so that electrostatic discharge will not occur from one to the other. This connecting trace is then cut just before inserting the device into the measurement cell.

For silicon nitride nanopores without nanoelectrodes, aggressive cleaning in hot piranha solution may be used to refresh devices. Caution: piranha is a strong oxidizer that reacts violently with most organic materials. An ionizing air blower, for example, Simco-Ion Model 5802i (Simco-Ion, Hatfield, Pa., USA), may also help to prevent electrostatic buildup. Nanopore devices may be subjected to rapid thermal annealing (MILA-5000, ULVAC Technologies, Methuen, Mass., USA, ramp to 350° C. in 1 min, hold at 350° C. for 1 min, then allow to cool, all in a nitrogen forming gas atmosphere) and/or plasma cleaning (Solarus Model 950, Gatan, Warrandale, Pa., USA, 1 min, 6.4 sccm $H_2$, 27.5 sccm $O_2$, 70 mTorr, 50 W) directly after removal from the TEM, and then stored in 70% ethanol until they are used in an experiment.

Summary

Provided here are insulated nanoelectrodes on membranes (e.g., low-capacitance membranes, e.g., those made from silicon nitride) having nanopores disposed between the electrodes. The nanoelectrodes may be insulated, but may also have exposed tips so as to localize the sensing region for measurements in electrolyte solution. Insulation may be accomplished by atomic layer deposition and, leakage current measurements showed the effectiveness of this approach. By performing ionic current measurements using macroscopic electrodes, it was shown that the presence of nanoelectrodes and insulation do not affect the stability of the ionic current flowing through these pores, nor do they affect the characteristics of DNA translocation.

What is claimed:

1. A macromolecule analysis component, comprising:
   a substrate having an upper surface surmounted by a layer of a first material that comprises silicon dioxide, borosilicate glass, fused silica, quartz, or any combination thereof, the substrate defining a thickness in the range of from about 5 nm to about 1000 nm;
   a layer of a second material surmounting the layer of the first material;
   two metallic electrodes surmounting the layer of second material and an adhesion material disposed between the two metallic electrodes and the layer of second material, the two metallic electrodes having ends separated at least in part by an aperature, and
   at least one of the two metallic electrodes being at least partially surmounted by an insulating material,
   the aperture having an edge and extending through the layer of first material, through the layer of second material, and through the insulating material,
   the aperture's edge being defined by the layer of first material, the layer of second material, the insulating material, and the ends of the metallic electrodes, and
   wherein a first of the two metallic electrodes is in eletrical commnunication with a first conductive pad, wherein a second of the two metallic electrodes is in electrical communication with a second conductive pad, and wherein the first conductive pad and the second conductive pad are capable of electrical communication with one another through an electrically-conductive trace present on the component.

2. The macromolecule analysis component of claim 1, wherein the ends of the two metallic electrodes are separated by less than about 100 nm.

3. The macromolecule analysis component of claim 2, wherein the ends of the two metallic electrodes are separated by from about 2.5 to about 30 nm.

4. The macromolecule analysis component of claim 1, wherein the substrate comprises silicon.

5. The macromolecule analysis component of claim 1, wherein the first material comprises silicon dioxide.

6. The macromolecule analysis component of claim 1, wherein the second material comprises silicon nitride, aluminum oxide, hafnium oxide, silicon dioxide, or any combination thereof.

7. The macromolecule analysis component of claim 1, wherein the aperture has a cross-sectional dimension in the range of from about 0.5 nm to about 10 nm.

8. The macromolecule analysis component of claim 1, wherein the insulating material comprises titanium dioxide, aluminum oxide, hafnium oxide, or any combination thereof.

9. The macromolecule analysis component of claim 1, wherein the insulating material is present at least a thickness of one atomic layer.

10. The macromolecule analysis component of claim 1, wherein the substrate has a lower surface surmounted by a second layer of the first material.

11. The macromolecule analysis component of claim 10, wherein the second layer of the first material is surmounted by a second layer of the second material.

12. The macromolecule analysis component of claim 1, wherein the aperture in the layer of second material is in fluid communication with an aperture formed in the substrate.

13. The macromolecule analysis component of claim 1, wherein the two metallic electrodes are characterized as having tip regions adjacent to the aperture, the tip regions being free of the insulating material.

14. The macromolecule analysis component of claim 1, wherein the substrate defines a thickness in the range of from about 30 nm to about 70 nm.

15. The macromolecule analysis component of claim 1, wherein the insulating material defines a thickness in the range of from about 1 nm to about 50 nm.

16. The macromolecule analysis component of claim 1, wherein the substrate defines a thickness that is greater than the thickness of the layer of first material or the thickness of the layer of second material.

17. A method, comprising:
translocating a macromolecule through the aperture of a macromolecule analysis component, the macromolecule analysis component comprising:
a substrate having an upper surface surmounted by a layer of a first material that comprises silicon dioxide, borosilicate glass, fused silica, quartz, or any combination thereof, the substrate defining a thickness in the range of from about 5 nm to about 1000 nm;
a layer of a second material surmounting the layer of the first material;
two metallic electrodes surmounting the layer of second material and an adhesion material disposed between the two metallic electrodes and the layer of second material, the two metallic electrodes having ends separated at least in part by an aperture, and
at least one of the two metallic electrodes being at least partially surmounted by an insulating material,
the aperture having an edge and extending through the layer of first material, through the layer of second material, and through the insulating material,
the aperture's edge being defined by the layer of first material, the layer of second material, the insulating material, and the ends of the metallic electrodes, and
wherein a first of the two metallic electrodes is in eletrical communicatin with a first conductive pad, wherein a second of the two metallic electrodes is in electrical communication with a second conductive pad, and wherein the first conductive pad and the second conductive pad are capable of electrical communication with one another through an electrically-conductive trace present on the component, and
collecting a signal related to the translocation.

* * * * *

UNITED STATES PATENT AND TRADEMARK OFFICE
CERTIFICATE OF CORRECTION

PATENT NO. : 10,876,157 B2
APPLICATION NO. : 14/429655
DATED : December 29, 2020
INVENTOR(S) : Drndic et al.

Page 1 of 1

It is certified that error appears in the above-identified patent and that said Letters Patent is hereby corrected as shown below:

In the Claims

Column 12, Claim 9, Line 42, Replace:
"wherein the insulating material is present at least a thickness"
With:
--wherein the insulating material is present at a thickness--

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*